United States Patent [19]

Ammann et al.

[11] Patent Number: 5,604,204
[45] Date of Patent: Feb. 18, 1997

[54] METHOD OF INDUCING BONE GROWTH USING TGF-β

[75] Inventors: Arthur J. Ammann, San Rafael; Christopher G. Rudman, San Francisco, both of Calif.

[73] Assignee: Genentech, Inc., South San Francisco, Calif.

[21] Appl. No.: 395,939

[22] Filed: Feb. 27, 1995

Related U.S. Application Data

[62] Division of Ser. No. 132,405, Nov. 12, 1993, Pat. No. 5,409,896, which is a continuation of Ser. No. 63,841, May 18, 1993, abandoned, which is a continuation of Ser. No. 790,856, Nov. 12, 1991, abandoned, which is a division of Ser. No. 401,906, Sep. 1, 1989, Pat. No. 5,158,934.

[51] Int. Cl.$^6$ .......................... A61K 38/00; C12N 15/00; C07K 14/00
[52] U.S. Cl. ............................. 514/12; 514/2; 514/13; 514/21; 530/324; 530/350; 530/353
[58] Field of Search ............................. 514/2, 12, 13, 514/21; 530/324, 350, 353

[56] References Cited

U.S. PATENT DOCUMENTS

| | | | |
|---|---|---|---|
| 4,563,350 | 1/1986 | Nathan et al. | 424/549 |
| 4,642,120 | 2/1987 | Nevo et al. | 424/94.64 |
| 4,702,734 | 10/1987 | Terranova | 604/54 |
| 4,774,228 | 9/1988 | Seyedin | 514/21 |
| 4,774,322 | 9/1988 | Seyedin | 514/21 |
| 4,810,691 | 3/1989 | Seyedin | 514/21 |
| 4,843,063 | 6/1989 | Seyedin | 514/21 |
| 4,863,732 | 9/1989 | Nathan | 514/21 |
| 4,919,939 | 4/1990 | Baker | 514/21 |
| 4,968,590 | 11/1990 | Kuberasampath | 422/220 |
| 5,158,934 | 10/1992 | Amman et al. | 514/13 |
| 5,409,896 | 4/1995 | Amman et al. | 514/13 |

FOREIGN PATENT DOCUMENTS

| | | |
|---|---|---|
| 169016 | 1/1986 | European Pat. Off. . |
| 182483 | 5/1986 | European Pat. Off. . |
| 200341 | 12/1986 | European Pat. Off. . |
| 267463 | 5/1988 | European Pat. Off. . |
| 268561 | 5/1988 | European Pat. Off. . |

OTHER PUBLICATIONS

Ammann et al., "Transforming Growth-Factor-Beta-Effect on Soft Tissue Repair" *NY Acad. Sci. Meeting* (May 18, 1989).

Antosz et al., "Transforming Growth Factor-Beta (TFG-β) Inhibits Osteoblastic Differentiation and Bone Formation In Vitro" *J. Dent. Res.* 67(983):235 (1988).

Bauer et al., "Stimulation of in vitro human skin collagenase expression by platelet-derived growth factor" *Proc. Natl. Acad. Sci. USA* 82:4132–4136 (1985).

Bentz et al., "Cartilage Induction and Differentiation: The Role of Bone Derived Cartilage Inducing Factor (CIF-A)" *UCLA Symp. Mol. Cell. Biol.* pp. 137–147 (1987).

Bentz et al., "Purification of an Osteoinductive Factor from Bovine Demineralized Bone" *Journal of Cell Biology* 107(abstract 918):162a (1989).

Bolander et al., "Role of TGF–β in Fracture Repair" NY Acad. Sci. (May 1989).

Brown et al., "Enhancement of Wound Healing by Topical Treatment with Epidermal Growth Factor" *New England J. of Medicine* 321(2): 76–79 (1989).

Burger et al., "TGF–62 1 Inhibits Osteoclast Formation in Embryonic Mouse Long Bone Rudiments" *Calcif. Tiss. Int.* S–32(F3).

Canalis et al., "Isolation of Growth Factors from Adult Bovine Bone" *Calif. Tiss. Int.* 43:346–351 (1988).

Carrington et al., "Accumulation, Localization, and Compartmentation of Transforming Growth Factor β During Endochondral Bone Development" *Journal of Cell Biology* 107:1969–1975 (1988).

Centrella et al., "Human Platelet–Derived Transforming Growth Factor–β Stimulates Parameters of Bone Growth in Fetal Rat Calvariac" *Endocrinology* 119:2306–2312 (1986).

Centrella et al., "Skeletal tissue and transforming growth factor β" *FASEB J.* 2:3066–3073 (1988).

Centrella et al., "Transforming Growth Factor Beta Mediates Cell Replication but not Osteoblast Differentiation in Fetal Rat Calvariae" *Journal of Cell Biology* 101(245A):930 (1985).

Centrella et al., "Transforming Growth Factor β Is a Bifunctional Regulator of Replication and Collagen Synthesis in Osteoblast–enriched Cell Cultures from Fetal Rat Bone" *Journal of Biological Chemistry* 262:2869 2874 (1987).

Centrella et al., "Transforming Growth Factor β Regulates Osteoblast Replication and Type I Collagen Synthosis by Independent Means" *Journal of Cell Biology* 103(444a):1656 (1966).

Cheifetz et al., "The Transforming Growth Factor β System, a Complex Pattern of Cross—Reactive Ligands and Receptors" *Cell* 48:409–415 (1987).

Chenu et al., "TFG–β is a Potent Inhibitor of Osteoclast–Like Cell Formation Acting At Multiple Stages of Osteoclast Development" *Calcif. Tiss. Int.* 42(A10): 39 (1988).

(List continued on next page.)

Primary Examiner—Elizabeth C. Weimar
Assistant Examiner—P. Lynn Touzeau
Attorney, Agent, or Firm—Janet E. Hasak

[57] ABSTRACT

A method is provided for generation of bone at a site of an animal where skeletal tissue is deficient comprising administering to the animal, locally at the bone site in the presence of a source of osteogenic cells, an effective amount of a composition comprising TGF-β in a pharmaceutically acceptable carrier, provided that such composition excludes a bone morphogenetic cofactor, the composition being administered in an amount effective to induce bone growth at the bone site. Also provided is a device for implantation into a site of an animal where skeletal tissue is deficient comprising a device treated with an effective amount of a composition comprising TGF-β and a source of osteogenic cells in a pharmaceutically acceptable carrier.

7 Claims, 3 Drawing Sheets

OTHER PUBLICATIONS

Chenu et al., "Transforming growth factor β inhibits formation of osteoclast like cells in long term human marrow cultures" *Proc. Natl. Acad. Sci. USA* 85:5683–5687 (1988).

Cotugno et al., "Transforming Growth Factor Beta (TFG–β) is a Chemoattractant for Poziodontal Ligament Cells" *J. Dental Res.* 67(185):581 (1988).

D'Souza et al., "Transforming Growth Factor Beta (TGF–β) Resorbs Bone and is Produced by Osteoblast like Bone Cells" *J. Bone and Min. Res.* 1(abstract 65): 74 (1986).

Dernyck et al., "A new type of transforming growth factorβ. TGFβ3" *EMBO Jour.* 7(12):3737–3743 (1988).

Derynck et al., "Human transforming growth factor–β complementary DNA sequence and expression in normal and transformed cells" Nature 316:701–705 (Aug. 22, 1985).

Derynck et al., "Intron–exon structure of the human transforming growth factor–β precurson gene" Nucleic Acids Research 15(7):3188–3189 (1987).

Derynck et al., "The Murine Transforming Growth Factor–β Precursor" *Journal of Biological Chemistry* 261(10):4377–4379 (1986).

Derynck et al., "Sequence of the porcine transforming growth factor type B gene family" *Nucl. Acids Res.* 15:3187 (1987).

Edwards et al., "Transforming growth factor beta modulates the expression of collagcilasc and metalloproteinase inhibitor" *EMBO Journal* 6(7):1899–1904 (1987).

Elford et al., "Transforming Growth Factor–β Reduces the Phenotypic Expression of Osteoblastic MC3T3 E1 Cells in Monolayer Culture" *Bone* 8:259–262 (1987).

Globus et al., "Regulation of Bovine Bone Cell Proliferation by Fibroblast Growth Factor and Transforming Growth Factor β" *Endocrin.* 123:98–105 (1988).

Guenther et al., "Effects of Transforming Growth Factor Type Beta Upon Bone Cell Populations Grown Either in Monolayer or Semisolid Medium" *J. Bone and Min. Res.* 3(3):269–278 (1988).

Hanks, et al., "Amino acid sequence of the BSC–3 cell growth inhibitor (polyergin deduced from the nucleotide sequence of the cDNA" *Proc. Natl. Acad. Sci. USA* 85:79–82 (1988).

Harrod et al., "Effect of Transforming Growth Factor β on Osteoblast–like Cells" *Calcif. Tiss. Int.* 38(s16):62 (1985).

Hauschka et al., "Growth Factors in Bone Matrix" *Journal of Biological Chemistry* 261(27): 12665–12674 (1986).

Hayward et al., "Mechanisms of bone loss: rheumatoid arthritis, periodontal disease and osteoporosis" *Agents & Actions* 22:251–254 (1987).

Heine et al., "Role of Transforming Growth Factor–β in the Development of the Mouse Embryo" *Journal of Cell Biology* 105:2861–2876 (1987).

Hiraki et al., "Effect of transforming growth factor β cell proliferation and glycosaminoglycan synthesis by rabbit growth–plate chondrocytos in culture" *Biochimica et Biophysica Acta* 969:91–99 (1988).

Hock et al., "Transforming Growth factor Beta (TGF–Beta–1) Stimulates Bone Matrix Apposition and Bone Cell Replication in Cultured Rat Calvaria" *Calcif. Tiss. Int.* 42(A32:124 (1988).

Hollinger et al., "Influence of Exogenous Growth Factors on Osteogenin induced Bone Formation" *J. Dent. Res.* 68(abstract 611):258 (1989).

Ibbotson et al., "Effects of Transforming Growth Factors β1 and β2 on a Mouse Clonal. Osteoblastlike Cell Line MC3T3–E1" *J. Bone and Min. Res.* 4(1):37–45 (1989).

Ibbotson et al., "Human recombinant transforming growth factor α stimulates bone resorption and inhibits formation in vitro" *Proc. Natl. Acad. Sci. USA* 83:2228–2232 (1986).

Ibbotson et al., "Transforming Growth Factors and Bone" *UCLA Symp. Mol. Cell. Biol.* pp. 349–363 (1987).

Ibbotson et al., "Transforming Growth Factors and Bone" *J. Cell. Biochem. Supp.* 10H(abstract. H15):108 (1986).

Ibbotson et al., "Tumor Derived Growth Factor Increases Bone Resorption in a tumor Associated with Humoral Hypercalcemia of Malignancy" *Science* 221:1292–1294 (1983).

Ignotz et al., "Transforming Growth Factor–β Stimulates the Expression of Fibronectin and Collagen and Their Incorporation into the Extracellular Matrix" *The Journal of Biological Chemistry* 261(9):4337 4345 (Mar. 25, 1986).

Jakowlew et al., "Complementary Deoxyribonucleic Acid Cloning of a Messenger Ribonucleic Acid Encoding Transforming Growth Factor–β4 from Chicken Embryo Chondrocytes" *Molecular Endocrinology* 2:1186–1195 (1988).

Jakowlew et al., "Complementary Deoxyribonucleic Acid Cloning of a Novel Transforming Growth Factor–β Messenger Ribonucleic Acid from Chick Embryo Chondrocytes" *Molecular Endocrinology* 2(8):747–755 (1988).

Jennings et al., "Comparison of the Biological Actions of TGF Beta–1 and TGF Beta 2: Differential Activity in Endothelial Cells" *J Cell. Phys.* 137:167–172 (1988).

Joyce et al., "Transforming Growth Factor–β Initiates Bone and Cartilage Formation in Rat Periosteum" *ASHMR/ICCRH Joint Meeting* (1989).

Kawamura et al., "Growth Factors, Mitrogens, Cytokines, and Bone Morphogenetic Protein in Induced Chondrogenesis in Tissue Culture" *Dev. Biol.* 130:435–442 (1988).

Keski–Oja et al., "Transforming Growth Factors and Control of Neoplastic Cell Growth" *J. Cell. Biochem.* 33:95–107 (1987).

Komm et al., "Estrogen Binding, Receptor mRNA, and Biologic Response in Osteoblast–Like Osteosarcoma Cells" *Science* 241:81–84 (1988).

Linkhart et al., "Characterization of Mitogenic Activities Extracted from Bovine Bone Matrix" *Bone* 7:479–487 (1986).

Madisen et al., "Transforming Growth Factor–β2: cDNA cloning and Sequence Analysis" *DNA* 7(1):1–8 (1988).

Mundy. "Identifying Mechanisms for Increasing Bone Mass" *J. NIH Res* 1:65–68 (1989).

Mundy, "The Role of the Bone–Derived Factor TFG β in Bone Coupling" *J. Dent. Res.* 67(108):S47 (1988).

Noda, "Transcriptional Regulation of Osteocalcin Production by Transforming Growth Factor–β in Rat Osteoblast–Like Cells" *Endocrinology* 124(2):612–617 (1989).

Noda, "Transcriptional Regulation of Osteopontin Production in Rat Osteosarcoma Cells by Type β Transforming Growth Factor" *Journal of Biological Chemistry* 263 (27):13916–13921 (1988).

Noda et al., "In vivo Stimulation of Bone Formation by Transforming Growth Factor–β" *Endocrinology* 124(6):2991–2994 (1989).

Noda et al., "Transforming Growth Factor Type β Promotes Bone Formation In Vivo" Journal of Cell Biology 107(abstract 251):48a (1988).

Noda et al., "Type B Transforming Growth Factor (TGF β) Regulation of Alkaline Phosphatase Expression and Other Phenotype–Related mRNAs in Osteoblastic Rat Osteosarcoma Cells" *J. Cell Phys.* 133:426–437 (1987).

Noda et al., "Type–β Transforming Growth factor Inhibits Proliferation and Expression of Alkaline Phosphatase in Murine Osteblast–like Cells" *Biochem. & Biophys. Res. Comm.* 140 (1):56–65 (1986).

Oreffo et al., "Osteoclasts Activate Latent Transforming Growth Factor Beta and Vitamin A Treatment Increases TGF β Activation" *Calcif. Tiss. Int.* 42(Suppl.):A15 (1988).

Petkovich et al., "1,25–Dihydroxyvitamin D3 Increases Epidermal Growth Factor Receptors and Transforming Growth Factor β–Like Activity in a Bone–derived Cell Line" *Journal of Biological Chemistry* 262:13424–13428 (1987).

Pfeilschifter et al., "Effects of Transforming Growth Factor–β on Osteoblastic Osteosarcoma Cells" *Endocrinology* 121(1):212–218 (1987).

Pfeilschifter et al., "Modulation of type β transforming growth factor activity in bone cultures by osteotropic hormones" *Proc. Natl. Acad. Sci. USA* 84:2024–2028 (1987).

Pfeilschifter et al., "TFGβStimulates Osteoblast Activity and is Released During the Bone Resorption Process" *Calcium Regulation and Bone Metabolism* 9:450–454 (1987).

Pfeilschifter et al., "Transforming Growth Factor Beta (TFG–β) Inhibits Bone Resorption in Fetal Rat Long Bone Cultures" *J. Clin. Inv.* 82:680–685 (1988).

Pfeilschifter et al., "Transforming Growth Factor Beta (TFG–β) Inhibits Bone Resorption in Fetal Rat Long Bones" *Calcif. Tiss. Int.* 133(A34).

Pfeilschifter et al., "Transforming Growth Factor β (TFG–β) Increases Insulin–like Factor I (IGF–I) Secretion in Osteoblast–Like Cells" *Acta Endocrinologica (Supplement)* 120(1): 144–145 (1989).

Roberts et al., "Peptide Growth Factors and Their Receptors–I" *Handbook of Experimental Pharmacology*, Spron et al., Heidelberg:Springer–Verlag, Chapter 8, vol. 95(1) 1990).

Roberts et al., "Transforming growth factor type beta: potential intrinsic mediator of remodeling and repair of bone and cartilage" *Journal of Cell Biology* (abstract 34) 103(5 Part 2):624a, 10a (1986).

Roberts et al., "Transforming Growth factor β: Biochemistry and Roles in Embryogenesis. Tissue Repair and Remodeling, and Carcinogensis" *Recent Progress in Hormone Res.* 44:157–197 (1988).

Robey, "The Effect of Transforming Growth Factor–β on Human Bone Cells In Vitro" *Calcif. Tiss. Int.* 135(A34).

Robey et al., "Osteoblasts Synthesize and Respond to Transforming Growth Factor–Type β (TGF–β) in Vitro" *Journal of Cell Biology* 105:457–463 (1987).

Rodan et al., "Effect of Growth Factors on Calvaria and Ros 17/2.8 Cells" *Calcif. Tiss. Int.* 41(14):Orio (1987).

Rosen, "TGF–β and Bone Induction" *NY Acad. Sci. Mtg.* abstract (May 1989).

Rosen et al., "Repression of Osteoblast and Chondroblast Phenotypes in Vitro by Transforming Growth Factor–β/Cartilage Inducing Factor–A" *Journal of Cell Biology* 103(446a):1661 (1986).

Rosen et al., "Transforming Growth Factor–Beta Modulates the Expression of Osteoblast and Chondroblast Phenotypes in Vitro" *J. Cellular Physiology* 134:337–346 (1988).

Russell, "The Cellular Control of Bone Formation and Resorption" *J. Dental Res.* 66(S38):99 (1987).

Sampath et al., "Isolation of osteogenin, an extraceullular matrix–associated, bone–inductive protein, by heparin affinity chromatography" *Proc. Natl. Acad. Sci.* 84:7309–7113 (1987).

Sandberg et al., "Enhanced expression of TGF–β and c–fos mRNAs in the growth plates of developing human long bones" *Development* 102:461–470 (1988).

Sandberg et al., "Localization of the Expression of Types I, III, and IV Collagen, TGF–β1 and c–fos Genes in Developing Human Calvarial Bones" *Development Biology* 130:324–334 (1988).

Schultz et al., "Epithelial Wound Healing Enhanced by Transforming Growth Factor α and Vaccinia Growth Factor" *Science* 235:350–352 (1987).

Seyedin et al., "Cartilage Induction and Differentiation – The Role of bone Derived Cartilage Inducing Factor (CIP)" *J. Cell. Bioichem. Suppl.* 108(abstract H9):105 (1986).

Seyedin et al., "Cartilage–inducing Factor–A: Apparent Identity to Transforming Growth Factor–β" *J. Biological Chem.* 261(13):5693–5695 (1986).

Seyedin et al., "Cartilage–inducing Factor–β Is a Unique Protein Structurally and Functionally Related to Transforming Growth Factor–β" *J. Biological Chem.* 262(5):1946–1949 (1987).

Seyedin et al., "Purification and characterization of two cartilage–inducing factors from bovine demineralized bone" *Proc. Natl. Acad. Sci.* 82:2267–2271 (1985).

Sharples et al., "Cloning and Sequence Analysis of Simian Transforming Growth Factor–β cDNA" *DNA* 6(3):239–244 (1987).

Simpson, "Growth factors which affect bone" *Trends Biochem. Sci.* 9:527:530 (1984).

Sodek et al., "TGF–β Effects on Connectivo Tissue Cells: A Role for TGF–β in Wound Healing and Bone Remodelling" *J. Dental Res.* 66:191 Abstracts 676 (1987).

Sporn et al., "Peptide growth factors are multifunctional" *Nature* 332:217–219 (1988).

Sporn et al., "Polypeptide Transforming Growth Factors Isolated from Bovine Sources and Used for Wound Healing in vivo" *Science* 219:1329–1331 (1983).

Sporn et al., "Some Recent Advances in the Chemistry and Biology of Transforming Growth Factor Beta" *Journal of Cell Biology* 105:1039–1045 (Sep. 1987).

Stashenko et al., "Opposing Regulatory Effects of IL–1β and Bone Growth Factors on Bone Formation" *J. Dental Res.* 68(Symp V–VI):192 Abstract B4 (1989).

Tashjian, Jr. et al., "αand β human transforming growth factors stimulate prostaglandin production and bone resorption in cultured mouse calvaria" *Proc. Natl. Acad. Sci.* 82:4535–4538 (1985).

ton Dijke et al., "identification of another member of the transforming growth factor type β gene family" *Proc. Natl. Acad. Sci. USA* 85:4715–4719 (1988).

Terek et al., "Transforming Growth Factor–Beta Suppresses Cartilage Specific Gene Expression in Endochondral Bone Repair" *Clinical Research* 37(2):462A (1989).

Terranova et al., "A Biochemical Approach to Periodontal Regeneration. AFSCM: Assays for Specific Cell Migration" *J. Peridontol* 58(4):247–257 (1987).

Terranova et al., "A biochemical approach to peridontal regeneration: Tetracycline treatment of dentin promotes fibroblast adhesion and growth" *Journal of Peridontal Research* 21:330–337 (1986).

Terranova et al., "Chemotaxis of Human Gingival Epithelial Cells to Laminin: A Mechanism for Epithelial Cell Apical Migration" *J. Periodontol* 57(5): 311–317 (1986).

Terranova et al., "Extracellular Matrices and Polypeptide Growth Factors as Mediators of Functions of Cells of the Periodontium" *J. Periodontal* 58(6):371–380 (1987).

Terranova V. P. et al., "Biochemically mediated periodontal regeneration" *Journal of Periodontal Research* 22(3):248–251 (May 1987).

Uneno et al., "Transforming Growth Factor β Modulates Proliferation of Osteoblastic Cells: Relation to Its Effect on Receptor Levels for Epidermal Growth Factor" *J. Bone and Min. Res.* 4(2):165 171 (1989).

Valentin–Opran et al., "Resorption and formation in metastatic bone" *Rev Rhum Mal Osteourtic* 51(11):627–632 (abstract only) (1984).

Wakley et al., "Mitogens Produced by Human Bone Cells and Their Potential Role in the Development of a Bone Implant" *Non–Cemented Total Hip Arthroplasty*, Fitzgerald Jr., NY:Raven Press, Chapter 10, pp. 99–109 (1988).

Wang et al., "Purification and characterization of other distinct bone–inducing factors" *Proc. Ntal. Acad. Sci.* 85:9484–9488 (1988).

Williams et al. *Stedman's Medical Dictionary*, 24th edition, Baltimore, MD:Waverly Press pp. 1003–1006; 1054; 1058 (1982).

Wolf et al., "Transforming growth factor beta (TGF–β) is chemotactic for osteoblast–like cells" *Acta Endocrinologica* (Supplement: Abstract 260) 120(1):242 (1989).

Wozney et al., "Novel Regulators of Bone Formation: Molecular Clones and Activities" *Science* 242(16):1528–1534 (1988).

Wrana et al., "Differential Effects of Transforming Growth Factor–β on the Synthesis of Extracellular Matrix Proteins by Normal Fetal Rat Calvarial Bone Cell Populations" *Journal of Cell Biology* 106:915–924 (1988).

```
                    1          10          20          32          40         50
Hu TGF-β 1   MPPSGLRLLLPLLLPLLLWLLV-LTPGPPAAGLSTCKTIDMELVKRKRIEAIR
Hu TGF-β 2   MHYCVLSAFLILHLV---TVAL------S-LSTCSTLDMDQFMRKRIEAIR
Hu TGF-β 3   MKMHLQRALVVLALLNFATVSL------S-LSTCTTLDFGHIKKKRVEAIR 60         70         80         90
Hu TGF-β 1   GQILSKLRLASPPSQGE-VP-PGPLPEAVLALYNSTRDRVAGESAEPE-PE
Hu TGF-β 2   GQILSKLKLTSPP----EDYPEPEEVPPEVISIYNSIYNSTRDLL--QEKASR-RA
Hu TGF-β 3   GQILSKLRLTSPP---EPTV-MTHVPYQVLALYNSTRELL--EEHGER-KE
Ck TGF-β 4   ---------------------------------M--DPMSIGPK- 100        110        120        130
Hu TGF-β 1   P------EADYYAKEVTRVLMV----ETHNEIYDKFKQSTHSIYMFFNTS
Hu TGF-β 2   AACERERSDEEYYAKEVYKIDMPPFFPS-EHAIPPTFYRPY-FRIVRFDVS
Hu TGF-β 3   EGCTQENTESEYYAKEIHKFDMIQGLAE-HNELAVCPKGIT-SKVFRFNVS
Ck TGF-β 4   -SCG---------------GSPW-RPP-GTAPWSIG-SR--RATAS 140        150        160        170
Hu TGF-β 1   EL-----RE-AVPEPVLLS-RAELRLLRLKL----KV-EQHVELYQ----
Hu TGF-β 2   A------------MEKNASNLV-KAEFRVFRLQNPK-ARVPEQRIELYQILKSK
Hu TGF-β 3   S-------VEKNRTNLF-RAEFRVLRVPNPS-SKRNEQRIELFQILRP-
Ck TGF-β 4   SSCSTSSRVRAEVGGRALLHRAELRMLRQKAAADSAGTEQRLELYQGYGN- 180        190        200        210        220
Hu TGF-β 1   KYSNNSWRYLSNRLLAPSDSPEWLSFDVTGVVRQWLSRGGEIEGFRLSAHC
Hu TGF-β 2   DLTSPTQRYIDSKVVKTRAEGEWLSFDVTDAVHEWLHHKDRNLGFKISLHC
Hu TGF-β 3   DEHIAKQRYIGGKNLPTRGTAEWLSFDVTDTVREWLLRRESNLGLEISIHC
Ck TGF-β 4   ----ASWRYLHGRSVRATADDEWLSFDVTDAVHQWLSGSELLGVFKLSVHC
Fg TGF-β 5   -----------SDEWMSFDVTKTVNEWLKRAEENEQFGLQPAC
```

FIG. 1A

```
                        230           240           250
Hu TGF-β 1  SC--------DSRDNTLQVDIN-GFTTGR------RGDLATI--------
Hu TGF-β 2  PCCTFVPSNNYIIPNKSEELEARFA-GIDGTSTYTSGDQKTIKSTRKKNSG
Hu TGF-β 3  PCHTFQP-NGDILENIHEVMEIKFK-GVDNEDDHGRGDLGRLK---KQKDH
Ck TGF-β 4  PCEMGPG-HADEMRISIEGFEQQ---------------RGDMQSIA---K-KHR
Fg TGF-β 5  KCPT-PQ-AKDI-D--IEGFPAL---------------RGDLASLSS--KEN---

260           270           280           290
Hu TGF-β 1  HGMNRPFLLLMATPLERA-QH--LQSS---RHRRALDTNYCF--SSTEKNC
Hu TGF-β 2  KT---PHLLLMLLPSYRL-ESQ---QTNRRKKRALDAAYCF--RNVQDNC
Hu TGF-β 3  H--N-PHLILMMIPPHRL-DNPGQGGQ---RKKRALDTNYCF--RNLEENC
Ck TGF-β 4  R--V-PYVLAMALPAERANE---LHSA---RRRRDLDTDYCFGPGTDEKNC
Fg TGF-β 5  -TK--PYL--MIT-SMPAERIDTVTSS---RKKRGVGQEYCF--GNNGPNC 300           310           320           330           340
Hu TGF-β 1  CVRQLYIDFRKDLGWKWIHEPKGYHANFCLGPCPYIWSLDTQYSKVLALYN
Hu TGF-β 2  CLRPLYIDFRKDLGWKWIHEPKGYNANFCAGACPYLWSSDTQHSRVLSLYN
Hu TGF-β 3  CVRPLYIDFRQDLGWKWVHEPKGYYANFCSGPCPYLRSADTTHSTVLGLYN
Ck TGF-β 4  CVRPLYIDFRKDLQWKWIHEPKGYMANFCMGPCPYIWSADTQYTKVLALYN
Fg TGF-β 5  CVKPLYINFRKDLGWKWIHEPKGYEANYCLGNCPYIWSMDTQYSKVLSLYN 350           360           370           380           390
Hu TGF-β 1  QHNPGASAAPCCVPQALEPLPIVYYVGRKPKVEQLSNMIVRSCKCS
Hu TGF-β 2  TINPEASASPCCVSQDLEPLTILYYIGKTPKIEQLSNMIVKSCKCS
Hu TGF-β 3  TLNPEASASPCCVPQDLEPLTILYYVGRTPKVEQLSNMVVKSCKCS
Ck TGF-β 4  QHNPGASAAPCCVPQTLDPLPIIYYVGRNVRVEQLSNMVRACKCS
Fg TGF-β 5  QNNPGASISPCCVPDVLEPLPIIYYVGRTAKVEQLSNMVVRSCNCS
```

FIG. 1B

METHOD OF INDUCING BONE GROWTH USING TGF-β

This is a division of application Ser. No. 08/132,045 filed on 12 Nov. 1993, now U.S. Pat. No. 5,409,896 which is a continuation of Ser. No. 08/063,841 filed May 18, 1993, now abandoned, which is a continuation of Ser. No. 07/790,856 filed Nov. 12, 1991, now abandoned, which is a divisional of Ser. No. 07/401,906 filed Sep. 1, 1989, issued as U.S. Pat. No. 5,158,934.

BACKGROUND OF THE INVENTION

1. Field of the Invention

This invention relates to the use of transforming growth factor-beta to induce bone growth in vivo and to devices for implantation into a bony site that are treated with transforming growth factor-beta, as well as to pharmaceutical compositions for this purpose.

2. Description of Related Art

The disorders associated with bone loss present major public health problems for Western societies. Osteoporosis alone may affect 20 million Americans in the early years of the next century. Hence, there is wide interest in identifying factors or potential therapeutic agents that inhibit bone loss and stimulate the formation of healthy new bone.

Bone is an extremely complex, but highly organized, connective tissue that is continuously remodeled during the life of an adult by cellular events that initially break it down (osteoclastic resorption) and then rebuild it (osteoblastic formation). This remodeling process occurs in discrete packets throughout the skeleton, i.e., in both cortical bone and trabecular bone. It has recently been reported that mouse bone marrow cells can be stimulated to generate osteoclasts in the presence of parathyroid hormone-related protein or vitamin D. See Akatsu et al., *Endocrinology*, 125: 20–27 (1989); Takahashi et el., *Endocrinology*, 123: 2600–2602 (1988) and Takahashi et al., *Endocrinology*, 132: 1504–1510 (1988).

The currently available therapeutic agents known to stimulate bone formation are fluoride, estrogen, metabolites, and vitamin D. Fluoride clearly increases trabecular bone mass, but questions remain about the quality of the new bone formed, the side effects observed in some patients, whether there are beneficial effects on vertebral fracture rates, and whether increased fragility of cortical bone with subsequent propensity to hip fracture follows.

Another approach is using agents that promote resorption (parathyroid hormone) and then interrupt resorption (calcitonin). One proposed, but not validated, such sequential therapeutic regimen is coherence therapy, where bone metabolic units are activated by oral phosphate administration and then resorption is inhibited by either diphosphonates or calcitonin.

Within the past few years several factors that stimulate osteoblasts were identified in bone, including TGF-β, fibroblast growth factor, platelet-derived growth factor, insulin-like growth factor I, and β2 macroglobulin. Of these, TGF-β and IGF-I were deemed attractive candidates for factors linking previous bone resorption with subsequent bone formation. Mundy, *The Journal of NIH Research*, 1: 65–68 (1989).

Other proteins stored in the bone matrix may also be important for bone formation. When demineralized bone was injected into the muscle or subcutaneous tissue of rats, a cascade of events, including chondrogenesis, ensued. Urist, *Science*, 150: 893 (1965). This observed activity was due to bone morphogenetic protein (BMP). Since the 1960s several investigators have attempted to identify and characterize this activity. Thus, a protein of 22 Kd, called osteogenin, was identified that possessed the activity. Sampath et al., *Proc. Natl. Acad. Sci. USA*, 84: 7109 (1987). Recently, a glycoprotein called osteoinductive factor was purified that exhibited many of the same properties as TGF-β in vitro but which, unlike TGF-β, could induce all of the events involved in the osteoinductive process in vivo. Bentz et al., *J. Cell. Biol.*, 107: 162a (1989). Additionally, three proteins from demineralized ovine bone matrix were identified as having this activity. Wang et al., *Proc. Natl. Acad. Sci.*, 85: 9484 (1988) and Wozney et al., *Science*, 242: 1528 (1988). These proteins were named BMP-1, BMP-2A, and BMP-3, the latter two of which belong to the extended TGF-β family by limited sequence homology. These workers modified the assay for bone induction to show cartilage formation but did not show that the proteins ultimately stimulate formation of bone.

The transforming growth factor-beta (TGF-β) group of molecules are each dimers containing two identical polypeptide chains linked by disulfide bonds. The molecular mass of these dimers is about 25 Kd. Biologically active TGF-β has been defined as a molecule capable of inducing anchorage independent growth of target cell lines or rat fibroblasts in in vitro cell culture, when added together with EGF or TGF-α as a co-factor. TGF-β is secreted by virtually all cell types in an inactive form. This latent form can be activated by proteolytic cleavage of mature TGF-β from its precursor (at the Arg-Ala bond in position 278). A non-covalent complex is formed from the association of the mature TGF-β with the precursor remainder or with a protein binding to TGF-β or with alpha$_2$-macroglobulin. This complex is disrupted so as to activate the TGF-β either by exposure to transient acidification or by the action of exogenous proteases such as plasmin or plasminogen activator.

There are at least five forms of TGF-β currently identified, TGF-β1, TGF-β2, TGF-β3, TGF-β4, and TGF-β5. Suitable methods are known for purifying this family of TGF-βs from various species such as human, mouse, green monkey, pig, bovine, chick, and frog, and from various body sources such as bone, platelets, or placenta, for producing it in recombinant cell culture, and for determining its activity. See, for example, R. Derynck et al., *Nature*, 316:701–705 (1985): European Pat. Pub. Nos. 200,341 published Dec. 10, 1986, 169,016 published Jan. 22, 1986, 268,561 published May 25, 1988, and 267,463 published May 18, 1988; U.S. Pat. No. 4,774,322; Seyedin et al, *J. Biol. Chem.*, 262: 1946–1949 (1987); Cheifetz et al, *Cell*, 48: 409–415 (1987); Jakowlew et al., *Molecular Endocrin.*, 2: 747–755 (1988); Dijke et al., *Proc. Natl. Acad. Sci. (U.S.A.)*, 85: 4715–4719 (1988); Derynck et al., *J. Biol. Chem.*, 261: 4377–4379 (1986); Sharples et al., *DNA*, 6: 239–244 (1987); Derynck et al., *Nucl. Acids. Res.*, 15: 3188–3189 (1987); Derynck et al., *Nucl. Acids. Res.*, 15: 3187 (1987); Derynck et al., *EMBO J.*, 7: 3737–3743 (1988)); Seyedin et al., *J. Biol. Chem.*, 261: 5693–5695 (1986); Madisen et al., *DNA*, 7: 1–8 (1988); and Hanks et al., *Proc. Natl. Acad. Sci. (U.S.A.)*, 85: 79–82 (1988), the entire contents of these publications being expressly incorporated by reference.

TGF-β3, TGF-β4, and TGF-β5, which are the most recently discovered forms of TGF-β, were identified by screening cDNA libraries. None of these three putative proteins has been isolated from natural sources, although Northern blots demonstrate expression of the corresponding mRNAs. TGF-β4 and TGF-β5 were cloned from a chicken chondrocyte cDNA library (Jakowlew et al., *Molec. Endocrinol.*, 2: 1186–1195 (1988)) and from a frog oocyte cDNA library, respectively. The frog oocyte cDNA library can be screened using a probe derived from one or more sequences of another type of TGF-β. TGF-β4 mRNA is detectable in chick embryo chondrocytes, but is far less abundant than TGF-β3 mRNA in developing embryos or in chick embryo fibroblasts. TGF-β5 mRNA is expressed in frog embryos beyond the neurula state and in Xenopus tadpole (XTC) cells.

TGF-β has been shown to have numerous regulatory actions on a wide variety of both normal and neoplastic cells. TGF-β is multifunctional, as it can either stimulate or inhibit cell proliferation, differentiation, and other critical processes in cell function (M. Sporn, *Science*, 233:532 [1986]). For a general review of TGF-β and its actions, see Sporn et al., *J. Cell Biol.*, 105: 1039–1045 (1987) and Sporn and Roberts, *Nature*, 332: 217–219 (1988).

The multifunctional activity of TGF-β is modulated by the influence of other growth factors present together with the TGF-β. TGF-β can function as either an inhibitor or an enhancer of anchorage-independent growth, depending on the particular set of growth factors, e.g., EGF or TGF-α, operant in the cell together with TGF-β (Roberts et al., *Proc. Natl. Acad. Sci. U.S.A.*, 82:119 [1985]). TGF-β also can act in concert with EGF to cause proliferation and piling up of normal (but not rheumatoid) synovial cells (Brinkerhoff et al., *Arthritis and Rheumatism*, 26:1370 [1983]).

Although TGF-β has been purified from several tissues and cell types, as indicated above, it is especially abundant in bones (Hauschka et al., *J. Biol. Chem.*, 261: 12665 (1986)) and platelets (Assoian et al., *J. Biol. Chem.*, 258: 7155 (1983)). TGF-β is postulated to be one of the local mediators of bone generation and resorption, because of its presence in large amounts in bone and cartilage, because cells with osteoblast and chondrocyte lineage increase replication after exposure to TGF-β, and because TGF-β regulates differentiation of skeletal precursor cells. See Centrella et al., *Fed. Proc. J.*, 2: 3066–3073 (1988).

Immunohistochemical studies have shown that TGF-β is involved in the formation of the axial skeleton of the mouse embryo. TGF-β is also present in other embryos in the cytoplasm of osteoblasts in centers of endochondral ossification and in areas of intramembranous ossification of flat bones, such as the calvarium. Heine et al., *J. Cell. Biol.*, 105: 2861–2876 (1987). Following in situ hybridization of TGF-β1 probes, localization of TGF-β in both osteoclasts and osteoblasts has been described in development of human long bones and calvarial bones. Sandberg et al., *Development*, 102: 461–470 (1988), Sandberg et al., *Devel. Biol.*, 130: 324–334 (1988). TGF-β is found in adult bone matrix (Seyedin et al., *Proc. Natl. Acad. Sci. USA*, 82: 2267–2271 (1985), Seyedin et al., *J. Biol. Chem.*, 261: 5693–5695 (1986)) and appears at the time of endochondral ossification in an in vivo model of bone formation (Carrington et al., *J. Cell. Biol.*, 107: 1969–1975 (1988)). Cultured fetal bovine bone osteoblasts as well as rat osteosarcoma cells have high mRNA levels for TGF-β and secrete relatively high concentrations of TGF-β (Robey et al., *J. Cell. Biol.*, 105: 457–463 (1987)).

In certain in vitro models, TGF-β was found to stimulate the synthesis of collagen, osteopontin, osteonectin, and alkaline phosphatase, and to stimulate replication in osteoblast-like cells. See Centrella et al., *J. Biol. Chem.*, 262: 2869–2874 (1987), Noda et al., *J. Biol Chem.*, 263: 13916 (1988), Wrana et al., *J. Cell. Biol.*, 106: 915 (1988), Noda et al., *J. Cell. Physiol.*, 133: 426 (1987), Pfeilshifter et al., *Endocrinology*, 121: 212 (1987), Centrella et al., *Endocrinology*, 119: 2306 (1986), and Roby et al., *J. Cell. Biol.*, 105: 457 (1987). In other in vitro models, TGF-β was found to inhibit proliferation and expression of alkaline phosphatase and osteocalcin. See Centrella et al., supra, Noda and Rodan, *Biochem. Biophys. Res. Commun.*, 140: 56 (1986), and Noda, *Endocrinology*, 124: 612 (1989).

Further, while Centrella et al., supra, showed increased collagen synthesis after treatment of osteoblasts from rat calvaria with TGF-β, Robey et al., supra, could not show increased synthesis of collagen in fetal bovine bone osteoblasts, postulating that the increased collagen production is secondary to the effects of TGF-β on the proliferation of osteoblasts. In organ culture, TGF-β was reported to stimulate bone resorption in neonatal mouse calvarias, but inhibit resorption in the fetal rat long bone system. See Tashjian et al., *Proc. Natl. Acad. Sci. USA*, 82: 4535 (1981) and Pfeilshifter et al., *J. Clin. Invest.*, 82: 680 (1988). TGF-β activity was reported to be increased in cultures of fetal rat calvaria and in calvarial cells incubated with stimulators of bone resorption, such as parathyroid hormone, 1,25-dihydroxyvitamin $D_3$, and IL-1 (Petkovich et al., *J. Biol. Chem.*, 262: 13424–13428 (1987), Pfeilschifter and Mundy, *Proc. Natl. Acad. Sci USA*, 84: 2024–2028 (1987)). Furthermore, it was reported that TGF-β inhibits the formation of osteoclasts in bone marrow cultures. Chenu et al., *Proc. Natl. Acad. Sci. USA*, 85: 5683–5687 (1988). The showing that TGF-β has effects on both osteoclasts and osteoblasts led Pfeilschifter and Mundy, supra, to propose that it is involved in the strict coupling of the processes of bone resorption and bone formation characteristic of the remodeling process in adult bone. It has also been postulated that the local acidic, proteolytic environment provided by the osteoclasts results in activation of matrix-associated latent TGF-β. Oreffo et al., *Calcified Tiss. Internatl.*, 42: Suppl: A15 (1988).

In view of the conflicting results reported for in vitro activities, it is not clear whether in vitro models can be used to predict the effects of TGF-β on bone formation and resorption in vivo. See Roberts et al., *Proc. Natl. Acad. Sci. USA*, 82: 119 (1985).

Additional references reporting that TGF-β promotes the proliferation of connective and soft tissue for wound healing applications include U.S. Pat. No. 4,810,691 issued Mar. 7, 1989, U.S. Pat. No. 4,774,228 issued Sep. 27, 1988, Ignotz et al., *J. Biol. Chem,*, 261:4337 [1986]; J. Varga et al., *B. B. Res. Comm.*, 138:974 [1986]; A. Roberts et al., *Proc. Natl. Acad. Sci. U.S.A.*, 78:5339 [1981]; A. Roberts et al., *Fed. Proc.*, 42:2621 [1983]; and U.S. Pat. No. 4,774,228 to Seyedin et al. TGF-β stimulates the proliferation of epithelia (T. Matsui et al., *Proc. Natl. Acad. Sci. U.S.A.*, 83:2438 [1986]; G. Shipley et al. *Cancer Res.*, 46:2068 [1986]); induces collagen secretion in human fibroblast cultures (Chua et al., *J. Biol. Chem.*, 260:5213–5216 [1983]); stimulates the release of prostaglandins and mobilization of calcium (A. Tashjian et al., *Proc. Natl Acad. Sci. U.S.A.*, 82:4535 [1985]); and inhibits endothelial regeneration (R. Helmark et al., *Science*, 233:1078 [1986]).

In wound chambers implanted subcutaneously, TGF-β increased DNA and collagen production. Sporn et al., *Science*, 219:1329 (1983) and Sprugel et al., *Am. J. Pathol.*, 129: 601 (1987). Moreover, TGF-β produced collagen fibrosis when injected subcutaneously (Roberts et al., *Proc. Natl Acad. Sci, USA*, 83: 4167–4171 (1986)) and promoted healing of skin incisions in rats (Mutoe et al., *Science*, 237: 1333 (1987)). Nevertheless, although TGF-β induced chondrogenesis in muscle-derived cells in vitro (Seyedin et al., *Proc. Natl. Acad. Sci. USA*, 82: 2267 (1985) and Seyedin et al., *J. Biol. Chem.*, 261: 5693 (1986)), it did not produce cartilage in vivo even when implanted with collagenous substrates, a system used for a long time as a bone induction model in animals (Sampath et al., *Proc. Natl. Acad. Sci. USA*, 84: 7109 (1987) and Howes et al., *Calcif. Tissue Int.*, 42: 34 (1988)).

New studies have shown a time-dependent appearance of mRNA for TGF-β1 at a fracture site in a rat and have localized the peptide immunohistochemically in the periosteum of the healing fracture; the same researchers reported that injections of TGF-β1 into the periosteal area of the femur of young rats have caused significant formation of new cartilage. Bolander et al., *New York Academy of Sciences*, "Transforming Growth Factor-βs: Chemistry, Biology and Therapeutics", May 18–20, 1989. It has been found that injections of TGF-β1 into the parietal bone of young rats stimulated periosteal bone formation, resulting in a thickening of the calvarium. Noda et al., *J. Cell. Biol.*, 107: 48 (1988). TGF-β was reported to stimulate local periosteal woven bone formation when injected daily onto the periostea of parietal bones of neonatal rats. Noda and Camilliere, *Endocrinology*, 124: 2991–2994 (1989).

Certain researchers have found that TGF-β does not induce bone formation unless it is administered concurrently with a cofactor, e.g., an osteoinductive factor purified from bovine demineralized bone. Bentz et al., supra, U.S. Pat. No. 4,843,063 issued Jun. 27, 1989 to Seyedin et al., and U.S. Pat. No. 4,774,322 issued Sep. 27, 1988.

The above studies are inconclusive and inconsistent regarding the formation of mature, histologically normal bone with TGF-β alone. For example, the bones being generated by Noda et al., 1989, supra, were neonatal, i.e., not fully formed with large spaces and increased cartilage formation. In addition, woven bone is resorbed before mature bone is laid down. Thus there is still a demonstrated need for a bone induction agent that will induce bone only where it is needed, does not have side effects in some patients as does fluoride treatment, and does not require addition of a cofactor or another peptide growth factor for acceleration of repair of damaged bone in vivo.

Accordingly, it is an object of the present invention to provide exogenous TGF-β to a local site on an animal where skeletal (bony) tissue is deficient without administering a bone-inducing cofactor so as to produce in every case mature, morphologically normal bone at the site of administration where it is needed.

It is another object to provide a device for implantation into an animal for generation of bone that is treated with TGF-β in such a way as to induce bone at the implantation site.

These and other objects will become apparent to those skilled in the art.

SUMMARY OF THE INVENTION

The above objects are achieved by providing a method for generation of bone at a site of an animal where skeletal tissue is deficient comprising administering to the animal, locally at the site in the presence of an osteogenic cell source, an effective amount of a composition comprising TGF-β in a pharmaceutically acceptable carrier, provided that such composition excludes a bone morphogenetic cofactor, the composition being administered in an amount effective to induce bone growth at the site.

In another aspect, the invention provides a device for implantation into a site of an animal where skeletal tissue is deficient comprising a device treated with an effective amount of a composition comprising TGF-β and an osteogenic cell source in a pharmaceutically acceptable carrier.

In a still further aspect, the invention provides a pharmaceutical composition for treatment of a site of an animal where skeletal tissue is deficient comprising an effective amount of TGF-β and an osteogenic cell source in a pharmaceutically acceptable carrier.

These aspects of the invention enable the generation of normal mature bone every time only where it is required at a particular site, without having to add a specific bone-inducing cofactor to ensure bone formation. Preclinical results with TGF-β applied topically as described below show new bone formation in the presence of perichondrium in a rabbit, new bone formation surrounding ceramic implants in bone defects in a rat, and bone formation in a primate.

BRIEF DESCRIPTION OF THE DRAWINGS

FIGS. 1A and 1B illustrate the sequences of human TGF-β1 (SEQ ID NO.1), human TGF-β2 (SEQ ID NO.2), human TGF-β3 (SEQ ID NO. 3), chick TGF-β4 (SEQ ID NO.4), and frog TGF-β5 (SEQ ID NO.5).

DESCRIPTION OF THE PREFERRED EMBODIMENTS

Figure 2:
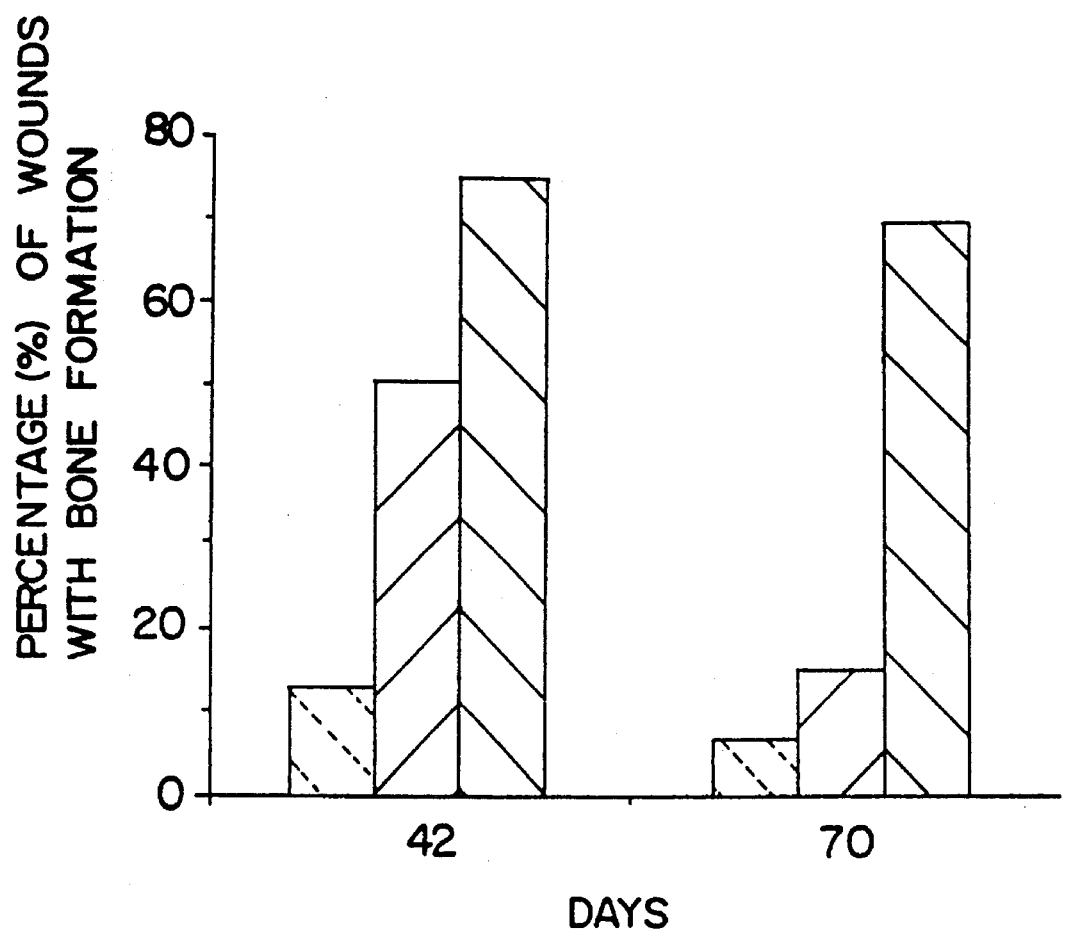
FIG. 2 illustrates the percentage of wounds with bone formation when placebo (left-most bar), recombinant human TGF-1 (rhTGF-β1) at 25 ng/wound (middle bar), or rhTGF-β1 at 100 ng/wound (right-most bar) is applied in the rabbit ear ulcer model at 42 and 70 days after wounding. Maximum bone formation was observed at day 42.

A. Definitions:

By "inducing bone growth" is meant promoting the formation of morphologically normal, mature bone only at a site where there is a bone deficiency that needs to be replaced. Mature bone is bone of any type, whether cortical or trabecular, that is mineralized as opposed to immature or cartilaginous bone as would be formed in a neonatal model. Morphologically normal bone is bone that is detected histologically as normal (i.e., consisting of endochondral or membranous type lamellar bone and including marrow spaces with osteoblasts and osteoclasts). This is in contrast, for example, to callous formation with a fibrotic matrix as seen in the first stage of fracture healing. Thus, the bone induction herein is contemplated not only as acceleration of bone regeneration, as in a fracture, but also as stimulation of the formation of bone that is returned to its normal morphological state.

By "skeletal tissue deficiency" is meant a deficiency in bone at any site where it is desired to restore the bone, no matter how bone deficiency originated, e.g., whether as a result of surgical intervention, removal of tumor, ulceration, implant, or fracture.

By "bone morphogenetic cofactor" is meant a protein originally found in the bone matrix that induces all of the cascade events involved in the osteoinductive process in vivo, including chondrogenesis, vascular invasion, formation of a marrow cavity, and eventually formation of a bone ossicle. Such factors include the bone morphogenetic proteins as found in demineralized bone (Urist, *Science*, 150: 893 (1965)), osteogenin, a 22 Kd protein with this activity (Sampath et al., *Proc. Natl. Acad. Sci. USA*, 84: 7109

(1987)), a glycoprotein called osteoinductive factor (U.S. Pat. No. 4,843,063, supra), and BMP-1, BMP-2A, and BMP-3 from demineralized ovine bone matrix (Wang et al, *Proc. Natl. Acad. Sci. USA*, 85: 9484 (1988) and Wozney et al., *Science*, 242: 1528 (1988)), the disclosures of all of which references are incorporated herein by reference.

The osteoinductive cofactor described in the U.S. patent is isolated from bone, preferably a bovine metatarsal bone, wherein the demineralized bone is prepared, noncollagenous proteins are extracted from the bone, the extract is subjected to gel filtration, the fraction constituting a low molecular weight (10,000–40,000 daltons) possessing the greatest chondrogenic activity is subjected to ion exchange chromatography, the first fraction CM-1 is subjected to RP-HPLC, and two peaks of predominantly 28 Kd and 36 Kd chondrogenic/osteogenic cofactor protein are purified to give single bands on SDS-PAGE. These cofactors and the others mentioned above are included in the term "bone morphogenetic cofactor."

By "osteogenic cell source" is meant a source of viable cells that are capable of forming bone, as well as viable cells that are precursors to cells capable of forming bone. Suitable such sources include dispersed whole bone marrow cells (obtained by, e.g., aspiration or mechanical agitation), perichondrium, periosteum, or a suitable cell line. For example, the cells may be taken from a site of the animal to be treated adjacent to the deficiency (e.g., periosteum stripped from an adjacent site to the defect such as a fracture site or a surgical excision site) or from a biopsy site of the animal (e.g., one that has been previously accessed, e.g., the hip).

By "animal" is meant any animal having a vertebrate structure, preferably a mammal, and most preferably a human.

By "TGF-β" is meant the family of molecules described hereinabove that have either the full-length, native amino acid sequence of any of the TGF-βs from any species, including the latent forms and associated or unassociated complex of precursor and mature TGF-β ("latent TGF-β"). Reference to such TGF-β herein will be understood to be a reference to any one of the currently identified forms, including TGF-β1, TGF-β2, TGF-β3, TGF-β4, and TGF-β5 and latent versions thereof, as well as to TGF-β species identified in the future, including polypeptides derived from the sequence of any known TGF-β and being at least 75% homologous with the sequence. Members of the TGF-β family are defined as those which have nine cysteine residues in the mature portion of the molecule, share at least 65% homology with other known TGF-β sequences in the mature region, and compete for the same receptor. In addition, they all appear to be encoded as a larger precursor that shares a region of high homology near the N-terminus and shows conservation of three cysteine residues in the portion of the precursor that will later be removed by processing. Moreover, the TGF-βs appear to have a four or five amino acid processing site.

B. Modes for Carrying Out the Invention

The invention is carried out in one aspect by mixing the TGF-β with a suitable pharmaceutical carrier, and without the bone morphogenetic cofactor, and administering the resulting composition locally to a site on an animal where it is desired to induce formation of normal, adult bone and where a source of osteogenic cells and their precursor cells are present at the site. If the site does not naturally have a source of osteogenic cells present, the pharmaceutical composition also contains an osteogenic cell source as defined above, in an amount sufficient to induce bone growth.

Examples of indications where promotion of bone repair at a skeletal site is important include periodontal disease where root socket healing is impaired (tooth socket sites), non-union fractures, including primary treatment of high risk fractures and adjunctive treatment with bone grafting or bone substitutes for established non-union fractures, large bony defects caused by trauma or surgery [e.g., partial mandibular resection for cancer, large cranial defects, spinal (vertebral) fusions, correction of severe scoliosis by surgical alignment held in place with a Harrington bar (to shorten the six months normally required for a body cast), and spinal fractures with open reduction (to decrease significantly the period of immobilization)], and rapid stabilization and enhanced fixation of artificial prostheses and spacer bars, oral joints, and bone replacements.

Examples of the latter include plastic and reconstructive surgery, fixation of permanent dentures into mandible, enhanced fixation of accepted Joint prosthesis, e.g., hips, knees, and shoulders (leading to the acceptance of prostheses that until now have been unacceptable due to rapid loosening and instability such as elbows), and limb salvage procedures, usually associated with malignancy (the bone shaft may be removed but the articular surfaces are left in place and connected by a space bar; rapid and enhanced fixation is required for success). If the site constitutes a periodontal site, i.e., one that involves the teeth, gums, and dental sockets, the TGF-β is administered in conjunction with an exogenously added source of osteogenic cells.

In one preferred embodiment, the TGF-β is administered by treating a device with the TGF-β composition and implanting the device into the animal at the site of the deficiency, the composition also containing the osteogenic cell source when the site is deficient in such cells. The device may consist of any device suitable for implantation, including a molded implant, plug, prosthetic device, capsule, titanium alloy, sponge, or ceramic block. Examples of suitable delivery vehicles useful as devices are those disclosed by Nade et al., *Clin. Orthop. Rel. Res.*, 181: 255–263 (1982); Uchida et al., *J. Biomed. Mat. Res.*, 21: 1–10 (1987); Friedenstein et al., *Exp. Hematol.*, 10: 217–227 (1982); Deporter et al., *Calcif. Tissue Int.*, 42: 321–325 (1988); McDavid et al., *J. Dent. Res.*, 58: 478–483 (1979); Ohgushi et al., *J. Orthopaedic Res.*, 7: 568–578 (1989), Aprahamian et al., *J. Biomed. Mat. Res.*, 21: 965–977 (1986); Emmanual et al., *Stain. Tech.*, 62: 401–409 (1987), the disclosure of all of which references is incorporated herein by reference.

For bone defects involving gaps, such as a dry socket or non-union fracture, a plug may be used to fill the gap. The plug may be composed of, for example, hydroxyapatite or collagen on which TGF-β is adsorbed. For larger bone defects resulting from, e.g., trauma or skeletal reconstruction around an ulcer or hip prosthesis, the device is preferably a made-to-fit ceramic block. More preferably, the ceramic block comprises 0–100% hydroxyapatite and the remaining 100–0% tricalcium phosphate, by weight, most preferably 60% hydroxyapatite and 40% tricalcium phosphate.

In a specific embodiment for a Jaw implant, a calcium carbonate moldable material or Interpore™ molding device is molded to fit the jaw using a 3-dimensional x-ray of the jaw before surgery, and the molded material is impregnated with TGF-β. Then, dispensed bone marrow from another site of the animal (e.g., from the hip) is infiltrated into the mold, and the mold is placed into the jaw for final implantation.

Preferably, the device is treated with the TGF-β composition (which includes both a solution and a gel formulation) for a sufficient period of time to allow adsorption, and to allow drying in the case of the gel. The concentration of TGF-β in the solution or gel and the time of exposure depend on a number of factors, including the volume of the defect, the potency of the TGF-β polypeptide, and the nature of the site to which it is applied, and will be adjusted accordingly. As the size of the defect increases, or when the site is other than a bone site, the concentration of TGF-β and the time of presoaking should be increased. The treatment is for preferably at least about 0.5 hour, depending on the factors mentioned above (more preferably at least about 1 hour, and most preferably 1–2 hours), before implantation. Also depending on the above considerations, the concentration of TGF-β in the TGF-β composition is preferably at least about 1 ng/ml (more preferably at least about 1–10 up to 100 ng/ml). The treatment may consist of any mode by which the composition is applied to the device to deliver effectively the TGF-β and the osteogenic cell source. Such treatment includes, for example, adsorption, covalent crosslinking, or impregnation, depending in part on the nature of the indication.

The TGF-β compositions to be used in the therapy will be dosed in a fashion consistent with good medical practice taking into account the nature of the skeletal tissue deficiency to be treated, the species of the host, the medical condition of the individual patient, the presence of any other cotreatment drug in the composition, the site of delivery of the agent, the method of administration, the scheduling of administration, and other factors known to practitioners. Because of differences in host response, significant site-to-site and patient-to-patient variability exists. For purposes herein, the "therapeutically effective amount" of TGF-β is an amount that is effective to induce bone growth, as defined above, at the site of skeletal tissue deficiency.

As a general proposition, the TGF-β is formulated and delivered to the target site at a dosage capable of establishing at the site a TGF-β level greater than about 0.1 ng/cc. Typically, the TGF-β concentrations range from about 0.1 ng/cc to 5 mg/cc, preferably from about 1 to 2000 ng/cc. These intra-tissue concentrations are maintained preferably by topical application and/or sustained release.

As noted above, these suggested amounts of TGF-β are subject to a great deal of therapeutic discretion. The key factor in selecting an appropriate dose and scheduling is the result obtained. Clinical parameters to determine an endpoint include increase in bone formation and mass and in radiographically detectable bone height. Such measurements are well known to those clinicians and pharmacologists skilled in the art.

The TGF-β composition is administered by any suitable means locally to the site, including topical and continuous release formulation. The active TGF-β ingredient is generally combined at ambient temperature at the appropriate pH, and at the desired degree of purity, with a physiologically acceptable carrier, i.e., a carrier that is non-toxic to the patient at the dosages and concentrations employed. The carrier may take a wide variety of forms depending on the form of preparation desired for administration.

To be effective, the TGF-β is converted by the body to its activated form, i.e., the mature form is cleaved from its precursor using a suitable enzyme and the resultant complex is treated with acid or other appropriate agent, to activate the TGF-β. Nevertheless, TGF-β is suitably administered in an inactive or delayed release form such as a complex of mature TGF-β to proTGF-β not containing mature TGF-β (i.e., the remaining precursor of TGF-β), to a TGF-β binding protein or to alpha$_2$-macroglobulin. The latent form is then converted to the active form either by naturally occurring mechanisms in the local environment or by formulation with TGF-β activating agents described above. See, e.g., Gentry et al., Mol. Cell. Biol., 8: 4162–4168 (1988); Miyazono et al., J. Biol. Chem., 263: 6407–6415 (1988); Wakefield et al., J. Biol. Chem., 263: 7646–7654 (1988); Keski-Oja et al., J. Cell Biochem. Suppl., 11A: 60 (1987); Kryceve-Martinerie et al., Int. J. Cancer, 35: 553–558 (1985); Lawrence et al., Biochem. Biophys. Res. Commun., 133: 1026–1034 (1985); Lawrence et al., J. Cell Physiol., 121: 184–188 (1984). Thus, the pH of the TGF-β composition may suitably reflect the conditions necessary for activation.

For the preparation of a liquid composition suitable for impregnation of a device, the carrier is suitably a buffer, a low molecular weight (less than about 10 residues) polypeptide, a protein, an amino acid, a carbohydrate including glucose or dextrans, a chelating agent such as EDTA, a cellulose, or other excipient. In addition, the TGF-β composition is preferably sterile. Sterility is readily accomplished by sterile filtration through (0.2 micron) membranes. TGF-β ordinarily will be stored as an aqueous solution, as it is highly stable to thermal and oxidative denaturation, although lyophilized formulations for reconstitution are acceptable.

Generally, where the bone disorder permits, one should formulate and dose the TGF-β for site-specific delivery, where the TGF-β is formulated into a sterile sustained-release composition suitable for local application to the desired site.

For local application of the TGF-β composition, for example, in the case of a bone defect that is a crack, e.g., a union fracture, the carrier may be any vehicle effective for this purpose. For obtaining a gel formulation, the liquid composition is typically mixed with an effective amount of a water-soluble polysaccharide, polyethylene glycol, or synthetic polymer such as polyvinylpyrrolidone to form a gel of the proper viscosity to be applied topically. The polysaccharide is generally present in a gel formulation in the range of 1–90% by weight of the gel, more preferably 1–20%. Examples of other suitable polysaccharides for this purpose, and a determination of the solubility of the polysaccharides, are found in EP 267,015, published May 11, 1988, the disclosure of which is incorporated herein by reference.

The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the TGF-β held within it.

Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight polyethylene glycols to obtain the proper viscosity. For example, a mixture of a polyethylene glycol of molecular weight 400–600 with one of molecular weight 1500 would be effective for this purpose when mixed in the proper ratio to obtain a paste.

The term "water soluble" as applied to the polysaccharides and polyethylene glycols is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

In a preferred embodiment, the gel contains about 2–5% by weight methylcellulose and the TGF-β is present in an amount of about 10–1000 μg per ml of gel. More preferably, the gel consists of about 3% methylcellulose by weight, lactic acid to pH 5.0, and 20–200 μg per ml of TGF-β. This corresponds to a dose of 1–10 μg of TGF-β per 50 μl of gel.

For the preparation of a sustained-release formulation, the TGF-β is suitably incorporated into a biodegradable matrix or microcapsular particle. A suitable material for this purpose is a polylactide, although other polymers of poly (α-hydroxycarboxylic acids), such as poly-D-(-)-3-hydroxybutyric acid (EP 133,988A), can be used. Additional biodegradable polymers include poly(lactones), poly(acetals), poly(orthoesters) or poly(orthocarbonates). The TGF-β is also suitably mixed with a biodegradable protein carrier such as collagen, atelocollagen, or gelatin to form a carrier matrix having sustained-release properties; the resultant mixture is then dried, and the dried material is formed into an appropriate shape, as described U.S. Pat. No. 4,774,091.

The initial consideration here must be that the carrier itself, or its degradation products, are non-toxic in the target bone site and will not further aggravate the condition. This can be determined by routine screening in animal models of the target bone disorder or, if such models are unavailable, in normal animals. For examples of sustained-release compositions, see U.S. Pat. No. 3,773,919, EP 58,481A, U.S. Pat. No. 3,887,699, EP 158,277A, Canadian Patent No. 1176565, U. Sidman et al., *Biopolymers*, 22:547 (1983), and R. Langer et al., *Chem. Tech.*, 12:98 (1982).

Controlled delivery of TGF-β to a site also is suitably accomplished using permeable hollow cellulose acetate fibers with the TGF-β and placed in the site and removed 24 hours later or left for longer periods of time (U.S. Pat. No. 4,175,326). Also, acrylic resin strips or cast films can be impregnated with TGF-β and applied to the affected site. In addition, narrow dialysis tubing can be filled with a TGF-β solution and placed so as to deliver TGF-β to the appropriate site.

The composition herein also may suitably contain other peptide growth factors such as IGF-I, TGF-α, human growth hormone, epidermal growth factor, and PDGF, provided that such factors do not include the bone morphogenetic factors defined above. Such growth factors are suitably present in an amount that is effective for the purpose intended, i.e., to promote formation of bone.

The invention will be more fully understood by reference to the following examples. They should not, however, be construed as limiting the scope of the invention. All literature citations are incorporated by reference.

EXAMPLE 1

The TGF-β1 used herein was the recombinant expression product of transfected human 293 cells as described by EP 200,341, supra, and by Derynck et al., *Nature*, 316: 701–705 (1985). The individual samples of recombinant human TGF-β1 (rhTGF-β1) were sterilely prepared in methylcellulose containing 20 mM sodium acetate buffer at pH 5.0 and applied as a single topical dose. Selected concentrations of rhTGF-β1 were mixed with methylcellulose gel so that the final concentration of methylcellulose was 3%. The vehicle was formulated in a similar manner without rhTGF-β1 as a control. The material was stored at 5° C. until use.

The rat incisional model utilized young adult Simonsen Albino rats (300–350 g). Full thickness skin incisions were made by cutting through the subdermal panniculus carnosus musculature following Betadine and 70% alcohol scrubbing to sterilize the wound. Two pairs of symmetrical transverse incisions (approximately 2.5 cm) were placed in each animal. A single dose of rhTGF-β1 in methylcellulose was placed into each stainless steel sutured wound by inserting a 25-gauge needle along the edge of the wound and below the sutures. The volume of rhTGF-β1 in 3% methylcellulose placed into each wound was 0.05 ml. Each rat had two incisions into which rhTGF-β1 in 3% methylcellulose was applied. One incision received either vehicle alone (3% methylcellulose) or no treatment at all. Concentrations of rhTGF-β1 were 500, 1000, 2000, or 4000 ng/ml. Dose response curves were developed using dose ranges of 5 to 10,000 ng/wound. Animals were euthanized on day 5, 7, 10, 14, 21, and 28. The entire dorsal skin was excised after the sutures were removed. Two 8-mm wide strips of skin were collected from each incision and fixed in 10% neutral buffered formalin for seven days.

New Zealand white male rabbits (2.5–2.8 kg) were purchased from Elkhorn rabbitry. Anesthesia was induced by an intramuscular injection of ketamine hydrochloride/xylazine hydrochloride mixture. After removal of hair from the ears, the area of the wound was sterilely prepared using Betadine with an alcohol rinse. A circular 6-mm punch biopsy instrument was used to produce wounds to the depth of the ear cartilage. The underlying perichondrium was removed with a periosteal elevator and fine scissors. Wounds were treated with 0.025 ml of 3% methylcellulose or 5, 15, 25, 100, 500, or 1000 ng of rhTGF-β1 in 3% methylcellulose (control). Opsite™ surgical dressing was placed over each wound. An Elizabethian collar was placed around the neck of the rabbits to prevent mechanical disruption of the wounds by the rabbit.

Studies were also designed to examine short-term and long-term effects of topical rhTGF-β1. Wounds were harvested on days 3, 5, 7, 14, 21, 28, 42, 56, and 70. Wounds were photographed, cut into hemisections, and fixed in 10% neutral buffered formalin for histology and morphometric analysis. Morphometric analysis included measurements of total healing wound area, closing wound area, upper wound gap, lower wound gap, area of collagen, area of granulation tissue, epithelial cell layer length, and bone formation. These measurements were made on the Bioquant System IV analyzer.

The rabbit ear ulcers were examined for delayed effects of rhTGF-β1 on days 21, 28, 42, 56, and 70 following a single application of 25 or 100 ng/wound on the day of wounding. Bone formation was observed along the wound edges and immediately adjacent to the cartilage. The bone was normal in morphological appearance, consisting of endochondral or membranous type bone and ossification with marrow spaces. Osteoblasts and osteoclasts were present. The percentage of wounds with bone increased to a maximum of 74% of the treated wounds at day 42 (100 ng/wound) and decreased to 69% by day 70. See FIG. 2. Bone formation was observed in less than 12% of placebo-treated wounds.

No bone formation was observed in the rat incision model, indicating that bone formation is induced only at a site that has a source of precursor (osteogenic) cells, in this case in the rabbit ear model where the wound was adjacent to perichondrium.

EXAMPLE 2

A rat femur gap model was employed wherein a polyethylene plate 2 mm thick, 8–10 mm long, and 4–5 mm wide was pinned to one face of a rat femur with stainless steel pins. From the center of the femur a 5–8 mm long piece of bone was removed. The plate serves to keep the gap in bone separated. This model is intended to mimic a nonunion fracture in a human.

Set into the gap in the femur is a porous cylindrical 200–400 micron ceramic implant of 60% by weight hydroxyapatite and 40% by weight tricalcium phosphate (Zimmer, Inc.), which is either (1) implant alone, (2) implant presoaked for 1 hour in a solution of 50 ng/ml TGF-β1 prepared as described in Example 1 and formulated in Delbecco's medium without serum, (3) implant plus dispersed whole bone marrow cells obtained from syngeneic rat, and (4) implant plus dispersed whole bone marrow cells pretreated with 50 ng/ml of the TGF-β1 in Delbecco's medium described above. A total of 15 rats were used for each of these four groups. One month after implant, the rats were sacrificed and analyzed for histological changes.

Preliminary results indicate that no bone replacement was observed in the control without cells or TGF-β nor with TGF-β without cells; TGF-β with cells was found to accelerate the rate of bone growth over cells alone. The bone formed with TGF-β was found in the interstices of the pores in the ceramic and bridged the gap. The bone formed with the TGF-β was found to be histologically normal.

EXAMPLE 3

A case study was performed using baboons to investigate the effect of TGF-β on bone wound healing. The baboon was selected because of the close analogy of its bone kinetics to those of man. A methylcellulose gel of TGF-β1 was delivered via an analytical bone implant, and after 22 days the implant was removed from the baboon. Tissue obtained from TGF-β implant sites was analyzed using quantitative histomorphometry to determine the mean effect of TGF-β on bone wound healing. Detailed non-quantitative histopathologic evaluation was also performed.

More specifically, four male baboons were implanted with four titanium analytical bone implants (cages) each, two per tibia in areas of close structural geometry. Holes were drilled in the tibia to allow implantation. After implantation, the baboons were allowed to heal for 41 days. On the 41st day, all the implant sites were surgically exposed, tissue was removed, and the test materials were implanted into the implant cores. Each animal received a normal (no treatment) control, a control with only methylcellulose vehicle, and a low (1 μg rhTGF-β in methylcellulose) or high (10 μg rhTGF-β in methylcellulose) dosage of active TGF-β. Specifically, these formulations each consisted of 1 g of 3.0% methylcellulose by weight, lactic acid QS to pH 5.0, and 0, 20, or 200 μg/ml of rhTGF-β1 prepared as described in Example 1. The formulations were poured into size 5 gelatin capsules (Elanco), which were then placed in the core of the titanium implant and used to deliver 50 μl of each formulation, with slow dissolution of the capsule. All implant sites within an animal were randomly assigned to one of the four treatments.

Following 22 days of healing, tissue in all implants was retrieved. The tissue samples were placed in 10% formalin solution, buffered to a pH of 7.0, containing formaldehyde at 3.7% for fixation. Samples were submitted for histopathologic analysis.

The following descriptive and quantitative observations were made:

1. Bone volume in TGF-β sites was lower than control and placebo sites, although not statistically significant.
2. Osteoblast numbers, volume, and activity were significantly greater in the TGF-β sites when compared to either the control or placebo.
3. Osteoclast numbers and activity appeared higher in all four treatment sites when subjectively compared to control data obtained in previous studies.
4. Residual methylcellulose was noted and appeared to require phagocytosis before new trabecular bone could form.
5. TGF-β in the presence of methylcellulose matrix was associated with increased numbers of fibroblast, osteoprogenitor cells, and osteoblasts.
6. No foreign body response or other adverse pathologic reaction to either matrix alone or matrix and TGF-β was observed.
7. Significant periosteal new bone formation was noted over the implants in five TGF-β sites in three animals. Bone formation over the implant to this degree had never been observed in over 450 titanium implant procedures carried out over the past few years.
8. TGF-β sites were identified during blinded histologic review in seven out of a total of eight sites.
9. Methylcellulose sites were identified during blinded histologic review 100% of the time.

Control samples analyzed in this study demonstrated that cancellous tissue formed in the titanium implant is stratified from inferior to superior aspects of the implant core. The superior portion of the tissue (closest to the cap of the titanium implant) is less mature and shows greater osteoblastic activity, while tissue near the inferior aspects of the implant and deep within the medullary compartment is more mature in morphology and shows a reduced osteoblastic population and activity. In contrast to historical and control samples, the TGF-β tissue samples were homogeneous in their high osteoblastic activity throughout the specimen.

Clinical observations of the tissue above and around the supra-periosteal portion of the titanium implant revealed pronounced periosteal bone formation. This periosteal bone formed large masses over two sites in each of two animals. The masses in these two animals were highly vascularized, had the clinical appearance of trabecular bone, and varied in size within one animal. The two masses in each of two animals were approximately 3×2×1.5 cm and 1.5×1×0.5 cm in size. One additional animal demonstrated pronounced periosteal bone formation over one TGF-β site. It is significant that in over 430 titanium implant surgical procedures masses like these have never formed over the titanium implants. Histologically, this periosteal bone formation over five TGF-β sites in three baboons was similar to an actively healing, uncomplicated, fracture callus, i.e., morphologically normal, mature bone formation.

In general, the methylcellulose was well tolerated and no foreign body response was present in any of the four treatment sites. Additionally, no evidence of cytologic atypia or malignancy was found in either titanium implants or periosteal samples.

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 390 amino acids
        ( B ) TYPE: amino acid
        ( D ) TOPOLOGY: linear ( x i ) SEQUENCE DESCRIPTION: SEQ ID NO:1:

```
Met Pro Pro Ser Gly Leu Arg Leu Leu Pro Leu Leu Leu Pro Leu
 1               5                  10                  15

Leu Trp Leu Leu Val Leu Thr Pro Gly Pro Pro Ala Ala Gly Leu
                20                  25                  30

Ser Thr Cys Lys Thr Ile Asp Met Glu Leu Val Lys Arg Lys Arg
                35                  40                  45

Ile Glu Ala Ile Arg Gly Gln Ile Leu Ser Lys Leu Arg Leu Ala
                50                  55                  60

Ser Pro Pro Ser Gln Gly Glu Val Pro Pro Gly Pro Leu Pro Glu
                65                  70                  75

Ala Val Leu Ala Leu Tyr Asn Ser Thr Arg Asp Arg Val Ala Gly
                80                  85                  90

Glu Ser Ala Glu Pro Glu Pro Glu Pro Glu Ala Asp Tyr Tyr Ala
                95                  100                 105

Lys Glu Val Thr Arg Val Leu Met Val Glu Thr His Asn Glu Ile
                110                 115                 120

Tyr Asp Lys Phe Lys Gln Ser Thr His Ser Ile Tyr Met Phe Phe
                125                 130                 135

Asn Thr Ser Glu Leu Arg Glu Ala Val Pro Glu Pro Val Leu Leu
                140                 145                 150

Ser Arg Ala Glu Leu Arg Leu Leu Arg Leu Lys Leu Lys Val Glu
                155                 160                 165

Gln His Val Glu Leu Tyr Gln Lys Tyr Ser Asn Asn Ser Trp Arg
                170                 175                 180

Tyr Leu Ser Asn Arg Leu Leu Ala Pro Ser Asp Ser Pro Glu Trp
                185                 190                 195

Leu Ser Phe Asp Val Thr Gly Val Val Arg Gln Trp Leu Ser Arg
                200                 205                 210

Gly Gly Glu Ile Glu Gly Phe Arg Leu Ser Ala His Cys Ser Cys
                215                 220                 225

Asp Ser Arg Asp Asn Thr Leu Gln Val Asp Ile Asn Gly Phe Thr
                230                 235                 240

Thr Gly Arg Arg Gly Asp Leu Ala Thr Ile His Gly Met Asn Arg
                245                 250                 255

Pro Phe Leu Leu Leu Met Ala Thr Pro Leu Glu Arg Ala Gln His
                260                 265                 270

Leu Gln Ser Ser Arg His Arg Arg Ala Leu Asp Thr Asn Tyr Cys
                275                 280                 285

Phe Ser Ser Thr Glu Lys Asn Cys Cys Val Arg Gln Leu Tyr Ile
                290                 295                 300

Asp Phe Arg Lys Asp Leu Gly Trp Lys Trp Ile His Glu Pro Lys
                305                 310                 315
```

```
Gly Tyr His Ala Asn Phe Cys Leu Gly Pro Cys Pro Tyr Ile Trp
                320                 325                 330

Ser Leu Asp Thr Gln Tyr Ser Lys Val Leu Ala Leu Tyr Asn Gln
                335                 340                 345

His Asn Pro Gly Ala Ser Ala Ala Pro Cys Cys Val Pro Gln Ala
                350                 355                 360

Leu Glu Pro Leu Pro Ile Val Tyr Tyr Val Gly Arg Lys Pro Lys
                365                 370                 375

Val Glu Gln Leu Ser Asn Met Ile Val Arg Ser Cys Lys Cys Ser
                380                 385                 390
```

( 2 ) INFORMATION FOR SEQ ID NO:2:

( i ) SEQUENCE CHARACTERISTICS:
        ( A ) LENGTH: 414 amino acids
        ( B ) TYPE: amino acid
        ( D ) TOPOLOGY: linear ( x i ) SEQUENCE DESCRIPTION: SEQ ID NO:2:

```
Met His Tyr Cys Val Leu Ser Ala Phe Leu Ile Leu His Leu Val
 1               5                  10                  15

Thr Val Ala Leu Ser Leu Ser Thr Cys Ser Thr Leu Asp Met Asp
                 20                 25                  30

Gln Phe Met Arg Lys Arg Ile Glu Ala Ile Arg Gly Gln Ile Leu
                 35                 40                  45

Ser Lys Leu Lys Leu Thr Ser Pro Pro Glu Asp Tyr Pro Glu Pro
                 50                 55                  60

Glu Glu Val Pro Pro Glu Val Ile Ser Ile Tyr Asn Ser Thr Arg
                 65                 70                  75

Asp Leu Leu Gln Glu Lys Ala Ser Arg Arg Ala Ala Ala Cys Glu
                 80                 85                  90

Arg Glu Arg Ser Asp Glu Glu Tyr Tyr Ala Lys Glu Val Tyr Lys
                 95                100                 105

Ile Asp Met Pro Pro Phe Phe Pro Ser Glu Asn Ala Ile Pro Pro
                110                 115                 120

Thr Phe Tyr Arg Pro Tyr Phe Arg Ile Val Arg Phe Asp Val Ser
                125                 130                 135

Ala Met Glu Lys Asn Ala Ser Asn Leu Val Lys Ala Glu Phe Arg
                140                 145                 150

Val Phe Arg Leu Gln Asn Pro Lys Ala Arg Val Pro Glu Gln Arg
                155                 160                 165

Ile Glu Leu Tyr Gln Ile Leu Lys Ser Lys Asp Leu Thr Ser Pro
                170                 175                 180

Thr Gln Arg Tyr Ile Asp Ser Lys Val Val Lys Thr Arg Ala Glu
                185                 190                 195

Gly Glu Trp Leu Ser Phe Asp Val Thr Asp Ala Val His Glu Trp
                200                 205                 210

Leu His His Lys Asp Arg Asn Leu Gly Phe Lys Ile Ser Leu His
                215                 220                 225

Cys Pro Cys Cys Thr Phe Val Pro Ser Asn Asn Tyr Ile Ile Pro
                230                 235                 240

Asn Lys Ser Glu Glu Leu Glu Ala Arg Phe Ala Gly Ile Asp Gly
                245                 250                 255

Thr Ser Thr Tyr Thr Ser Gly Asp Gln Lys Thr Ile Lys Ser Thr
                260                 265                 270

Arg Lys Lys Asn Ser Gly Lys Thr Pro His Leu Leu Leu Met Leu
```

```
                              275                           280                           285
Leu  Pro  Ser  Tyr  Arg  Leu  Glu  Ser  Gln  Gln  Thr  Asn  Arg  Arg  Lys
                    290                           295                           300

Lys  Arg  Ala  Leu  Asp  Ala  Ala  Tyr  Cys  Phe  Arg  Asn  Val  Gln  Asp
                    305                           310                           315

Asn  Cys  Cys  Leu  Arg  Pro  Leu  Tyr  Ile  Asp  Phe  Lys  Arg  Asp  Leu
                    320                           325                           330

Gly  Trp  Lys  Trp  Ile  His  Glu  Pro  Lys  Gly  Tyr  Asn  Ala  Asn  Phe
                    335                           340                           345

Cys  Ala  Gly  Ala  Cys  Pro  Tyr  Leu  Trp  Ser  Ser  Asp  Thr  Gln  His
                    350                           355                           360

Ser  Arg  Val  Leu  Ser  Leu  Tyr  Asn  Thr  Ile  Asn  Pro  Glu  Ala  Ser
                    365                           370                           375

Ala  Ser  Pro  Cys  Cys  Val  Ser  Gln  Asp  Leu  Glu  Pro  Leu  Thr  Ile
                    380                           385                           390

Leu  Tyr  Tyr  Ile  Gly  Lys  Thr  Pro  Lys  Ile  Glu  Gln  Leu  Ser  Asn
                    395                           400                           405

Met  Ile  Val  Lys  Ser  Cys  Lys  Cys  Ser
                    410                      414
```

( 2 ) INFORMATION FOR SEQ ID NO:3:

( i ) SEQUENCE CHARACTERISTICS:
    ( A ) LENGTH: 412 amino acids
    ( B ) TYPE: amino acid
    ( D ) TOPOLOGY: linear ( x i ) SEQUENCE DESCRIPTION: SEQ ID NO:3:

```
Met  Lys  Met  His  Leu  Gln  Arg  Ala  Leu  Val  Val  Leu  Ala  Leu  Leu
 1                  5                            10                           15

Asn  Phe  Ala  Thr  Val  Ser  Leu  Ser  Leu  Ser  Thr  Cys  Thr  Thr  Leu
                    20                           25                           30

Asp  Phe  Gly  His  Ile  Lys  Lys  Lys  Arg  Val  Glu  Ala  Ile  Arg  Gly
                    35                           40                           45

Gln  Ile  Leu  Ser  Lys  Leu  Arg  Leu  Thr  Ser  Pro  Pro  Glu  Pro  Thr
                    50                           55                           60

Val  Met  Thr  His  Val  Pro  Tyr  Gln  Val  Leu  Ala  Leu  Tyr  Asn  Ser
                    65                           70                           75

Thr  Arg  Glu  Leu  Leu  Glu  Glu  His  Gly  Glu  Arg  Lys  Glu  Glu  Gly
                    80                           85                           90

Cys  Thr  Gln  Glu  Asn  Thr  Glu  Ser  Glu  Tyr  Tyr  Ala  Lys  Glu  Ile
                    95                           100                          105

His  Lys  Phe  Asp  Met  Ile  Gln  Gly  Leu  Ala  Glu  His  Asn  Glu  Leu
                    110                          115                          120

Ala  Val  Cys  Pro  Lys  Gly  Ile  Thr  Ser  Lys  Val  Phe  Arg  Phe  Asn
                    125                          130                          135

Val  Ser  Ser  Val  Glu  Lys  Asn  Arg  Thr  Asn  Leu  Phe  Arg  Ala  Glu
                    140                          145                          150

Phe  Arg  Val  Leu  Arg  Val  Pro  Asn  Pro  Ser  Ser  Lys  Arg  Asn  Glu
                    155                          160                          165

Gln  Arg  Ile  Glu  Leu  Phe  Gln  Ile  Leu  Arg  Pro  Asp  Glu  His  Ile
                    170                          175                          180

Ala  Lys  Gln  Arg  Tyr  Ile  Gly  Gly  Lys  Asn  Leu  Pro  Thr  Arg  Gly
                    185                          190                          195

Thr  Ala  Glu  Trp  Leu  Ser  Phe  Asp  Val  Thr  Asp  Thr  Val  Arg  Glu
                    200                          205                          210
```

| | | | | | | | | | | | | | | |
|---|---|---|---|---|---|---|---|---|---|---|---|---|---|---|
| Trp | Leu | Leu | Arg | Arg<br>215 | Glu | Ser | Asn | Leu | Gly<br>220 | Leu | Glu | Ile | Ser | Ile<br>225 |
| His | Cys | Pro | Cys | His<br>230 | Thr | Phe | Gln | Pro | Asn<br>235 | Gly | Asp | Ile | Leu | Glu<br>240 |
| Asn | Ile | His | Glu | Val<br>245 | Met | Glu | Ile | Lys | Phe<br>250 | Lys | Gly | Val | Asp | Asn<br>255 |
| Glu | Asp | Asp | His | Gly<br>260 | Arg | Gly | Asp | Leu | Gly<br>265 | Arg | Leu | Lys | Lys | Gln<br>270 |
| Lys | Asp | Asn | Asn | Asn<br>275 | Pro | His | Leu | Ile | Leu<br>280 | Met | Met | Ile | Pro | Pro<br>285 |
| His | Arg | Leu | Asp | Asn<br>290 | Pro | Gly | Gln | Gly | Gly<br>295 | Gln | Arg | Lys | Lys | Arg<br>300 |
| Ala | Leu | Asp | Thr | Asn<br>305 | Tyr | Cys | Phe | Arg | Asn<br>310 | Leu | Glu | Glu | Asn | Cys<br>315 |
| Cys | Val | Arg | Pro | Leu<br>320 | Tyr | Ile | Asp | Phe | Arg<br>325 | Gln | Asp | Leu | Gly | Trp<br>330 |
| Lys | Trp | Val | His | Glu<br>335 | Pro | Lys | Gly | Tyr | Tyr<br>340 | Ala | Asn | Phe | Cys | Ser<br>345 |
| Gly | Pro | Cys | Pro | Tyr<br>350 | Leu | Arg | Ser | Ala | Asp<br>355 | Thr | Thr | His | Ser | Thr<br>360 |
| Val | Leu | Gly | Leu | Tyr<br>365 | Asn | Thr | Leu | Asn | Pro<br>370 | Glu | Ala | Ser | Ala | Ser<br>375 |
| Pro | Cys | Cys | Val | Pro<br>380 | Gln | Asp | Leu | Glu | Pro<br>385 | Leu | Thr | Ile | Leu | Tyr<br>390 |
| Tyr | Val | Gly | Arg | Thr<br>395 | Pro | Lys | Val | Glu | Gln<br>400 | Leu | Ser | Asn | Met | Val<br>405 |
| Val | Lys | Ser | Cys | Lys<br>410 | Cys | Ser<br>412 | | | | | | | | |

( 2 ) INFORMATION FOR SEQ ID NO:4:

( i ) SEQUENCE CHARACTERISTICS:
        ( A ) LENGTH: 304 amino acids
        ( B ) TYPE: amino acid
        ( D ) TOPOLOGY: linear ( x i ) SEQUENCE DESCRIPTION: SEQ ID NO:4:

| | | | | | | | | | | | | | | |
|---|---|---|---|---|---|---|---|---|---|---|---|---|---|---|
| Met<br>1 | Asp | Pro | Met | Ser<br>5 | Ile | Gly | Pro | Lys | Ser<br>10 | Cys | Gly | Gly | Ser | Pro<br>15 |
| Trp | Arg | Pro | Pro | Gly<br>20 | Thr | Ala | Pro | Trp | Ser<br>25 | Ile | Gly | Ser | Arg | Arg<br>30 |
| Ala | Thr | Ala | Ser | Ser<br>35 | Ser | Cys | Ser | Thr | Ser<br>40 | Ser | Arg | Val | Arg | Ala<br>45 |
| Glu | Val | Gly | Gly | Arg<br>50 | Ala | Leu | Leu | His | Arg<br>55 | Ala | Glu | Leu | Arg | Met<br>60 |
| Leu | Arg | Gln | Lys | Ala<br>65 | Ala | Ala | Asp | Ser | Ala<br>70 | Gly | Thr | Glu | Gln | Arg<br>75 |
| Leu | Glu | Leu | Tyr | Gln<br>80 | Gly | Tyr | Gly | Asn | Ala<br>85 | Ser | Trp | Arg | Tyr | Leu<br>90 |
| His | Gly | Arg | Ser | Val<br>95 | Arg | Ala | Thr | Ala | Asp<br>100 | Asp | Glu | Trp | Leu | Ser<br>105 |
| Phe | Asp | Val | Thr | Asp<br>110 | Ala | Val | His | Gln | Trp<br>115 | Leu | Ser | Gly | Ser | Glu<br>120 |
| Leu | Leu | Gly | Val | Phe<br>125 | Lys | Leu | Ser | Val | His<br>130 | Cys | Pro | Cys | Glu | Met<br>135 |

```
Gly Pro Gly His Ala Asp Glu Met Arg Ile Ser Ile Glu Gly Phe
            140                 145                 150

Glu Gln Gln Arg Gly Asp Met Gln Ser Ile Ala Lys Lys His Arg
            155                 160                 165

Arg Val Pro Tyr Val Leu Ala Met Ala Leu Pro Ala Glu Arg Ala
            170                 175                 180

Asn Glu Leu His Ser Ala Arg Arg Arg Arg Asp Leu Asp Thr Asp
            185                 190                 195

Tyr Cys Phe Gly Pro Gly Thr Asp Glu Lys Asn Cys Cys Val Arg
            200                 205                 210

Pro Leu Tyr Ile Asp Phe Arg Lys Asp Leu Gln Trp Lys Trp Ile
            215                 220                 225

His Glu Pro Lys Gly Tyr Met Ala Asn Phe Cys Met Gly Pro Cys
            230                 235                 240

Pro Tyr Ile Trp Ser Ala Asp Thr Gln Tyr Thr Lys Val Leu Ala
            245                 250                 255

Leu Tyr Asn Gln His Asn Pro Gly Ala Ser Ala Ala Pro Cys Cys
            260                 265                 270

Val Pro Gln Thr Leu Asp Pro Leu Pro Ile Ile Tyr Tyr Val Gly
            275                 280                 285

Arg Asn Val Arg Val Glu Gln Leu Ser Asn Met Val Val Arg Ala
            290                 295                 300

Cys Lys Cys Ser
            304
```

( 2 ) INFORMATION FOR SEQ ID NO:5:

( i ) SEQUENCE CHARACTERISTICS:
        ( A ) LENGTH: 199 amino acids
        ( B ) TYPE: amino acid
        ( D ) TOPOLOGY: linear ( x i ) SEQUENCE DESCRIPTION: SEQ ID NO:5:

```
Ser Asp Glu Trp Met Ser Phe Asp Val Thr Lys Thr Val Asn Glu
  1               5                  10                  15

Trp Leu Lys Arg Ala Glu Glu Asn Glu Gln Phe Gly Leu Gln Pro
            20                  25                  30

Ala Cys Lys Cys Pro Thr Pro Gln Ala Lys Asp Ile Asp Ile Glu
            35                  40                  45

Gly Phe Pro Ala Leu Arg Gly Asp Leu Ala Ser Leu Ser Ser Lys
            50                  55                  60

Glu Asn Thr Lys Pro Tyr Leu Met Ile Thr Ser Met Pro Ala Gly
            65                  70                  75

Arg Ile Asp Thr Val Thr Ser Ser Arg Lys Lys Arg Gly Val Gly
            80                  85                  90

Gln Glu Tyr Cys Phe Gly Asn Asn Gly Pro Asn Cys Cys Val Lys
            95                 100                 105

Pro Leu Tyr Ile Asn Phe Arg Lys Asp Leu Gly Trp Lys Trp Ile
            110                115                 120

His Glu Pro Lys Gly Tyr Glu Ala Asn Tyr Cys Leu Gly Asn Cys
            125                130                 135

Pro Tyr Ile Trp Ser Met Asp Thr Gln Tyr Ser Lys Val Leu Ser
            140                145                 150

Leu Tyr Asn Gln Asn Asn Pro Gly Ala Ser Ile Ser Pro Cys Cys
            155                160                 165

Val Pro Asp Val Leu Gly Pro Leu Pro Ile Ile Tyr Tyr Val Gly
```

|  | 170 | 175 | 180 |
|---|---|---|---|
| Arg Thr Ala Lys | Val Glu Gln Leu Ser<br>185 | Asn Met Val Val Arg Ser<br>190 | Ser<br>195 |
| Cys Asn Cys Ser<br>199 | | | |

What is claimed is:

1. A device for implantation into a site of an animal where skeletal tissue is deficient comprising a device treated with an effective amount of a composition comprising TGF-β and an osteogenic cell source in a pharmaceutically acceptable carrier excluding a bone morphogenetic cofactor.

2. The device of claim 1 wherein the TGF-β is TGF-β1 or TGF-β3.

3. The device of claim 1 wherein the osteogenic cell source is dispersed whole bone marrow, perichondrium, periosteum, or a cell line.

4. The device of claim 1 which is a molded implant, prosthetic device, capsule, titanium alloy, or ceramic block.

5. The device of claim 4 which is a ceramic block comprising 0–100% hydroxyapatite and the remaining 100–0% tricalcium phosphate, by weight.

6. The device of claim 5 wherein the ceramic block comprises 60% hydroxyapatite and 40% tricalcium phosphate.

7. The device of claim 1 wherein the treatment is by adsorption, covalent crosslinking, or impregnation.

* * * * *